(12) United States Patent
Douglas et al.

(10) Patent No.: US 6,379,915 B1
(45) Date of Patent: *Apr. 30, 2002

(54) DIAGNOSTIC COMPOSITIONS AND DEVICES UTILIZING SAME

(75) Inventors: Joel S. Douglas, Santa Clara; Karen R. Drexler, Los Altos Hills, both of CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,655

(22) Filed: Mar. 20, 2000

Related U.S. Application Data

(60) Continuation of application No. 09/273,532, filed on Mar. 22, 1999, now Pat. No. 6,040,151, which is a continuation of application No. 09/037,653, filed on Mar. 10, 1998, now Pat. No. 5,885,790, which is a division of application No. 08/628,794, filed on Apr. 5, 1996, now Pat. No. 5,776,719.

(51) Int. Cl.[7] .............. C12Q 1/28; C12Q 1/26; C12Q 1/54
(52) U.S. Cl. .............. 435/28; 435/25; 435/14; 435/4; 435/808; 435/18; 435/814; 435/970; 435/283.1
(58) Field of Search .............. 435/28, 25, 14, 435/4, 808, 18, 814, 970, 283.1

(56) References Cited

U.S. PATENT DOCUMENTS

| | | | |
|---|---|---|---|
| 3,964,871 A | 6/1976 | Hochstrasser | 435/28 |
| 4,059,407 A | 11/1977 | Hochstrasser | 435/28 |
| 4,101,381 A | 7/1978 | Klose et al. | 435/28 |
| 4,168,205 A | 9/1979 | Danninger et al. | 435/28 |
| 4,247,297 A | 1/1981 | Berti et al. | 435/28 |

(List continued on next page.)

FOREIGN PATENT DOCUMENTS

| | | |
|---|---|---|
| DE | 43 43 082 A1 | 6/1995 |
| EP | 0 007 787 | 2/1980 |
| EP | 328 029 | 8/1989 |
| EP | 0 735 369 | 10/1996 |
| GB | 938029 | 9/1963 |
| JP | 07311498 | 2/1995 |
| WO | 90/90/06372 | 6/1990 |

OTHER PUBLICATIONS

Chemical Abstract, 95:38761 (1981).
M. Mizoguchi, et al., Bunseki Kagaku, 45(2): 111–124 (1996) (and an English language abstract).
International Search Report, PCT/US97/1177, International Filing Date Jul. 7, 1997, mailed Nov. 12, 1997.

*Primary Examiner*—Louise N. Leary
(74) *Attorney, Agent, or Firm*—Burns, Doane, Swecker & Mathis LLP

(57) ABSTRACT

A dry chemistry dye indicator composition provides improved shelf life, stable color indication end point and capability for a system at near normal pH. The novel dry chemistry dye indication system comprises 3-Methyl-6-(sodium sulfonate)-benzothiazolinone-(2)-hydrazone (MBTH-S). A preferred dye systems are based on the dye couple (MBTH-S) and 8-anilino-1-naphthalenesulfonate (ANS), and the dye couple MBTH-S and N-(3-sulfopropyl) analine. These dye indicator systems are used in conventional blood chemistry test strips and are particularly preferred for indication of glucose in blood.

14 Claims, 1 Drawing Sheet

U.S. PATENT DOCUMENTS

| | | | |
|---|---|---|---|
| 4,247,631 A | 1/1981 | Nix et al. | 435/28 |
| 4,260,679 A | 4/1981 | Tsuda et al. | 435/28 |
| 4,278,439 A | 7/1981 | White | 435/28 |
| 4,367,285 A | 1/1983 | Yamaguchi et al. | 435/28 |
| 4,385,114 A | 5/1983 | Güthlein et al. | 435/28 |
| 4,416,983 A | 11/1983 | Röder et al. | 435/28 |
| 4,492,754 A | 1/1985 | Trager et al. | 435/28 |
| 4,605,629 A | 8/1986 | Lange et al. | 435/28 |
| 4,734,360 A | 3/1988 | Philips et al. | 435/28 |
| 4,820,632 A | 4/1989 | Frey et al. | 435/28 |
| 4,851,335 A | 7/1989 | Kerscher et al. | 435/28 |
| 5,059,394 A | 10/1991 | Phillips et al. | 435/28 |
| 5,082,626 A | 1/1992 | Grage, Jr. | 435/28 |
| 5,084,382 A | 1/1992 | Frey et al. | 435/28 |
| 5,304,468 A | 4/1994 | Phillips et al. | 435/28 |
| 5,306,623 A | 4/1994 | Kiser | 435/28 |
| 5,315,035 A | 5/1994 | Frey et al. | 435/28 |
| 5,334,508 A | 8/1994 | Hoenes | 435/28 |
| 5,453,360 A | 9/1995 | Yu | 435/28 |
| 5,526,120 A | 6/1996 | Jina et al. | 435/28 |
| 5,563,031 A | 10/1996 | Yu | 435/28 |
| 5,776,719 A * | 7/1998 | Douglas et al. | 435/28 |
| 5,885,790 A * | 3/1999 | Douglas et al. | 435/28 |
| 6,040,151 A * | 3/2000 | Douglas et al. | 435/28 |

* cited by examiner

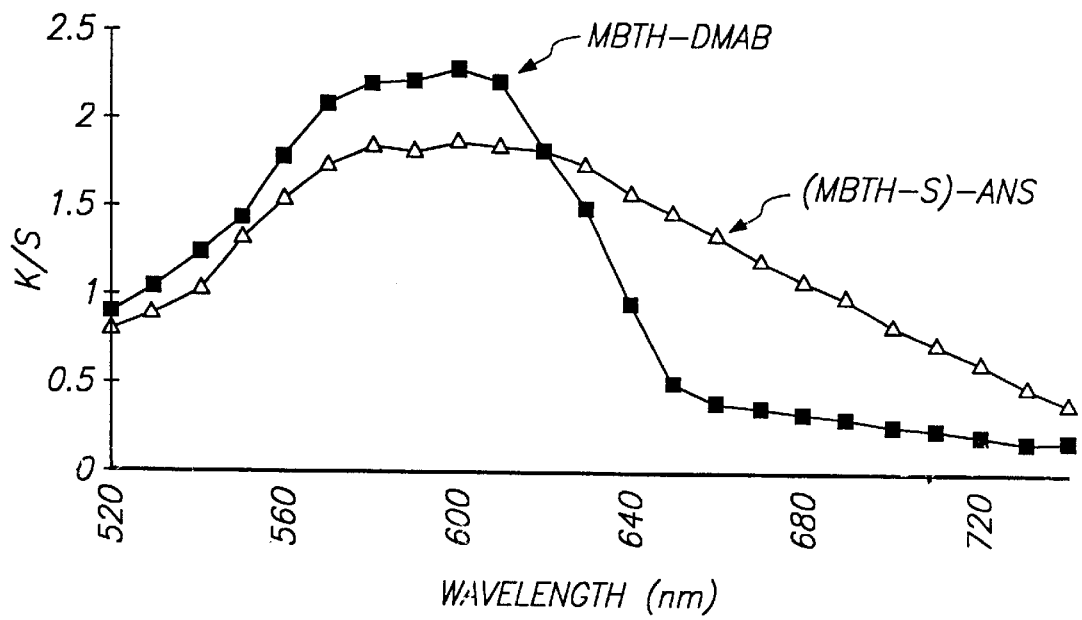
FIG. 1 COMPARISON OF DYE SPECTRA
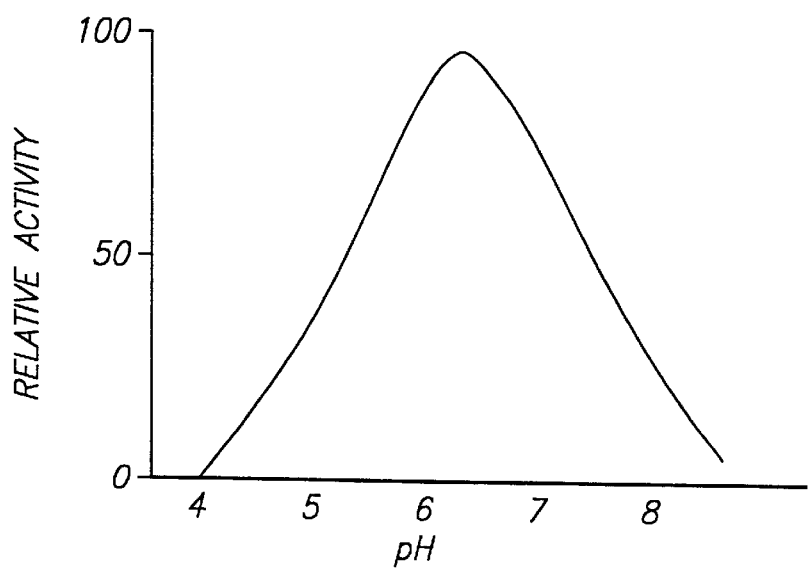
FIG. 2 pH vs. ACTIVITY

DIAGNOSTIC COMPOSITIONS AND DEVICES UTILIZING SAME

This application is a continuation, of Application Ser. No. 09/273,532, filed Mar. 22, 1999, now U.S. Pat. No. 6,040,151; which is a continuation of application Ser. No. 09/037,653, filed Mar. 10, 1998, now U.S. Pat. No. 5,885,790; which is a divisional of application Ser. No. 08/628,794 filed Apr. 5, 1996, now U.S. Pat. No. 5,776,719.

FIELD OF THE INVENTION

The present invention relates to dye compositions used for colorimetric determination of a chemical or biochemical component (analyte) in an aqueous body fluid, such as blood. In particular the present invention relates to the field of dry reagent compositions for use on test strips adapted to receive a liquid sample of body fluid whereby the dye indicator composition wetted by the fluid reacts with the analyte and provides a visual or color indication of the presence or concentration of the analyte.

BACKGROUND OF THE INVENTION

Indicator compositions for use in devices for color indication of various analytes in various body fluids are well known in the art and are embodied in numerous commercial products. Typically a dye composition or a dye couple composition is formulated in a solution which is applied to a test strip matrix then dried to form a dry chemistry system on the test strip. The dry chemistry system commonly involve an oxidizable dye or dye couple in combination with a oxidase or peroxidase specific to the analyte to be tested. The analyte reacts with the corresponding oxidase or peroxidase producing hydrogen peroxide which in turn oxidizes the dye or dye couple to produce the desired color change for indication of the presence or concentration of the analyte.

Example of such dye and dye couple systems are disclosed by Phillips et al. in U.S. Pat. Nos. 4,734,360; 5,059,394 and 5,304,468; by Yu in U.S. Pat. No. 5,453,360; Hoenes in U.S. Pat. No. 5,334,508 and by Hochstrasser in U.S. Pat. Nos. 3,964,871 and 4,059,407.

The disclosures of the above patents are incorporated herein by reference.

A number of the indicator systems disclosed in the above references are incorporated into various commercial products. While the products generally provide acceptable indication and testing under some conditions, certain problems exist with the prior dye systems. For example, in some dye systems the dry chemistry dye system existing on the test strip will allow the dye compounds to sublime from the test strip so that when the test strip is used by the consumer it may not provide an accurate indication. This limits the shelf life of the test strips. In some dye systems the color change provided by the dye system continues to change over time rather than reaching a stable end point. In those dye systems, the color indication must be accurately read at specific time intervals in order to obtain accurate indication of analyte presence or concentration. Some dye systems require a low pH to provide the necessary stability of the dye system. If the pH is below the desired pH level for stability of the enzymes used in the dye system the amount of enzymes used in the formulation must be increased. In such a case this can cause the enzymes to produce undesired indications due to the instability of the enzymes at the low pH required for the dye system.

In view of the above it is an object of this invention to provide an indicator dye system with improved stability to prevent sublimation of the dye system from the dry chemistry test strips.

It is an object of this invention to provide a dye system which will rapidly produce a stable end point thereby producing a final color indication in a short period of time thus eliminating the time dependent measurement or determination by the user.

It is a further object of this invention to provide a dye system which can be formulated and used a more normal pH to provide a more stable system for the enzymes present during the manufacture or use of the dye system.

The above objects as well as others are achieved by the compositions and systems of this invention as disclosed herein.

SUMMARY OF THE INVENTION

In one aspect this invention provides a dye composition comprising 3-methyl-6(M sulfonate)-benzothiazolinone-(2)-hydrazone (MBTH-S) where M is a positive ion providing a stable sulfonate salt and an oxidase enzyme or a peroxidase enzyme. This dye composition is formulated into a dry chemistry indicator system including other dye compounds to form dye couple system and conventional binders, chelating agents, buffers and the like, as known in the art. The MBTH-S is used in the composition in form of a stable sulfonate salt, of which the sodium salt is preferred, but the potassium, ammonium or other ionic form of the sulfonate salt may be used. In a preferred aspect of this invention the MBTH-S is used with another dye compound to form a dye couple for improved indication and a desired pH range in the range of about 6.

In another aspect this invention provides a device for testing a fluid for the presence or concentration of an analyte comprising a support for the dye composition wherein the dye composition comprises MBTH-S and an oxidase enzyme or a peroxidase enzyme as summarized above. The various mechanical configurations of such devices are known in the art and various configurations may be used incorporating the MBTH-S dye system of this invention adapted as desired for particular testing to be accomplished.

In another aspect this invention provides a method of testing a fluid for the presence or concentration of an analyte comprising contacting a fluid sample with a dry chemistry system comprising MBTH-S and an oxidase enzyme or a peroxidase enzyme as summarized above.

BRIEF DESCRIPTION OF THE DRAWINGS

FIG. 1 shows a comparison of the reflectance at certain light wavelengths of dye systems based on (MBTH-S)-ANS and based on MBTH-DMAB.

FIG. 2 is an illustration of the relative general activity of enzymes over a pH range.

DETAILED DESCRIPTION OF THE INVENTION

Dry chemistry indicator systems for use in test strips such as for testing for glucose in blood, are well known in the art as illustrated by the prior art patents referred to above in the background section of this specification. Therefore this disclosure is directed to one skilled in the art having knowledge of how to formulate a dye or dye couple composition into a dry chemistry reagent system on a test strip. The test strip typically is in the form of an absorbent matrix for containing the dry chemistry reagent indication system and for receiving the fluid sample to react with the dry chemistry reagent indicator system.

This invention provides an improved dye indicator system based on the use of 3-Methyl-6-(M sulfonate)-benzothiazolinone-(2)-hydrazone (MBTH-S), wherein M is a positive ion providing a stable sulfonate sale, preferably sodium, potassium, ammonium or other equivalent ion. Dry chemistry reagent dye systems formulated based on MBTH-S provide a dry chemistry system on test strips which are resistant to sublimation of the dye in the dry chemistry system and thus provide extended shelf life and increased reliability of the test strips containing the MBTH-S dye system. In addition, dry chemistry reagent dye systems formulated based on the MBTH-S of this invention can be formulated and buffered to operate in a pH range of about 6, which provides additional stability of the oxidise enzymes or peroxidase enzymes present in the dye indicator system. In addition, the dry chemistry reagent dye systems formulated based on the MBTH-S of this invention also provide a stable color reaction end point which is reached in a short period of time after applying the fluid sample. This enables the user to read and interpret the color indication without dependence on accurate timing or taking readings at specific time intervals, which usually requires the use of an electronic meter for accurate measurement and timing. This end point stability of the dye system of this invention also enables the use of the test strip as at least a semi-permanent record of the test results.

The dye systems of this invention are useful in prior art devices and systems including those involving the reaction of whole blood or other unfiltered fluid with the dry chemistry reagent dye system. In such devices and systems the color presence of whole blood obscures to visual inspection the indicator color change, but these systems can be read and measured by reflectance at certain specific light wavelengths by an appropriate electronic meter system. The dye systems according to this invention are particularly useful in devices and systems that separate the blood solids such as red blood cells from blood fluids and allow the clear blood fluids to contact and react with the dry chemistry reagent dye system, thus providing an unobscured, visually readable color change. In particular the dye system of the present invention is useful in the devices and systems disclosed in copending application Ser. No. 09/273532 filed Mar. 22, 1999, now U.S. Pat. No. 6,040,151, which disclosure is incorporated herein by reference.

In general it will be recognized by those skilled in the art that the MBTH-S dye system of this invention can be formulated and implemented in many of the dye systems previously based on MBTH by making the appropriate adjustment in buffer and other components to accommodate the different pH range and other properties of MBTH-S compared to the conventional MBTH.

The dry chemistry reagent dye system of this invention is formulated to enable to analyte to react with a specific oxidase enzyme to produce hydrogen peroxide which reacts with the MBTH-S indicator system according to this invention to produce a color change which is visually read or electronically measured with a meter. The oxidase enzyme may be selected from glucose oxidase, cholesterol oxidase, uricase, alcohol oxidase, aldehyde oxidase, glycerophosphate oxidase or other similar oxidase enzymes known in the art to be particularly reactive with a particular analyte. The system may also include the presence of a peroxidase enzyme such as horseradish peroxidase or other known peroxidase to produce or enhance the desired color change in the indicator. The indicator reagent dye system is formulated in a solution and is typically impregnated into a porous matrix or membrane such as a polyethersulfone membrane available from Gelman Science, Ann Arbor, Mich., or a fiberglass matrix available from AhlstromFiltration, Inc., chatanooga, Tenn., and dried to provide a dry chemistry system useful in the conventional test strips. The MBTH-S provided by this invention may be formulated in the dry chemistry reagent dye system alone or in combination with other dye components to form dye couple systems which preferably include 3,3-dimethylaminobenzoic acid (DMAB), 3,5-dichloro-2-hydroxybenzene-sulfonic acid (DCHBS), 8-anilino-1-naphthalenesulfonate (ANS), or N-(3-sulfopropyl)aniline. Other dye compounds which provide a sufficiently high extinction point (approx. 7.0 or higher is preferred) and which form an appropriate dye couple with MBTH-S can be used in the dye system of this invention. Formulation thereof will be apparent to one skilled in the art following the teachings herein. Reference is made to the Reagents Catalog from Dojindo Laboratories, Tokyo, Japan, and to a paper entitled "Reagents Used for Detecting Substances in Biological Matrix by Enzymatic Methods" published by Dojindo Laboratories at a 1995 Pacific Rim Conference, for dyes of appropriate properties for use in this invention.

By using MBTH-S and ANS a dye couple can be used which exists at a pH of 6 which permits the dye couple dry chemistry system to be used at this higher pH. It has been found that the MBTH-S and N-(3-sulfopropyl)aniline formulation is another preferred embodiment for the indicating dye system in the devices and methods of this invention. It creates a stable end point chemistry which is water soluble and does not sublime over time when applied and dried in the membrane matrix. The MBTH-S coupled with ANS provides flat spectral absorption in the region of about 580 to 650 nm. MBTH-S coupled with ANS provides good spectral absorption, is water soluble and does not sublime under dry chemistry storage conditions.

It will be apparent to one skilled in the art that the selection of the additional dye components to be combined with the MBTH-S or to provide dye couple systems with MBTH-S will depend on the analyte to be detected, the conditions under which the test strip is to be stored and used and other conventional considerations. However it has been found that the dye couple formed from the combination of MBTH-S and ANS provides a preferred dye couple system, particularly for formulation with glucose oxidase for glucose detection and measurement in blood fluids.

The preparation of 3-Methyl-6-(M sulfonate)-benzothiazolinone-(2)-hydrazone (MBTH-S) will be apparent to one skilled in the art as being the sulfonation of MBTH. The preferred MBTH-S is where M is Na. In this instance the sodium sulfonate salt is preferred and is prepared as follows. Reference can be made to Great Britain Patent No. 938,029 to Huenig for methods of sulfonation of dye compounds. 85 grams of 3-Methyl-benzothiazolinone-(2)-hydrazone (MBTH) is dissolved in 750 grams of 25% oleum situated in an ice bath so that the temperature is not allowed to exceed 30° C. Upon standing at room temperature for 12 hours complete solution is obtained. The solution is poured into 8 liters of 0° C. water containing excess ice to maintain the 0° C. temperature. Upon standing for about 8 hours the free sulfonic acid precipitate is filtered out, washed and dried. Approximately 85 grams of crude product is obtained, which is purified by repeat extractions with boiling methanol. The resulting solid is washed with water and dissolved in an equimolar amount of 3N NaOH with heating. This solution is filtered over activated charcoal and treated with a double volume of dioxane then allowed to crystallize overnight at about 5° C. The product is then subjected to repeated recrystallizations from 10% NaAcetate with concurrent activated charcoal filtration until the material is almost white. The final material is recrystallized from water and washed with 70% dioxane, then with pure dioxane, then with ether. The resulting crystals of 3-Methyl-6-(sodium sulfonate)-benzothiazolinone-(2)-hydrazone are air dried.

A dry chemistry reagent indicator dye system is formulated as follows: Test Reagents

| | |
|---|---|
| Reagent 1b | 20 ml water |
| | 420 mg citric acid (a buffering agent). Adjust th pH of the citric acid solution with NaOH to a value of 4.25. |
| | 16.7 mg EDTA |
| | 90 mg Gantrez S95 available from GAF |
| | 250 mg Crotein SPA |
| | 20,500 units glucose oxidase |
| | 16,200 units peroxidase |
| Reagent 2b | 10 ml of a mixture of 3 parts by volume water and 7 parts by volume isopropyl alcohol |
| | 13 mg MBTH-S |
| | 40 mg ANS |

A piece of polyethersulfone membrane from Gelman Science is uniformly coated with reagent 1 b; the excess is wiped off and the membrane dried. The membrane is then coated with reagent 2 b in the same fashion and dried. The membrane is then assembled into a test device as shown in FIG. 2 of copending application Ser. No.09/273,532 referred above. Whole blood is applied to the test area and the glucose level is read by visual inspection of the color indication on of the test side of the device. The color changes from clear to a purple to blue color and the final color end point forms from clear which is achieved in about 45 seconds and the end point color is calibrated to known concentrations of glucose.

FIG. 1 shows the comparative spectral reflective in the range of 520–720 nm for the dye system of the present invention based on a MBTH-S-ANS dye couple compared to a MBTH-DMAB dye couple, such as disclosed in Kiser U.S. Pat. No. 5,306,623.

FIG. 2 is a general illustration of the peroxidase activity of enzymes over a pH range as can be seen it is preferred to have systems which can operate closer to a pH between about 6 and 7. The dye system according to the present invention is stable at a buffered pH of about 6 thus enabling the dye system of this invention to operate in a pH range more favorable to the stability and activity of the oxidase anzymes and peroxidase enzymes present in the dye indicator system.

It will be apparent to one skilled in the art the MBTH-S dye indicator of this invention can be formulated in various systems with various oxidase and peroxidase material to provide desired indication of various analytes. It will also be apparent that the systems can be formulated at buffered pH levels which provide a favorable environment for stability of the enzyme components in the dry chemistry reagent system and in the fluid to be analyzed.

We claim:

1. A composition for a dry chemistry reagent indicator comprising:
   3-Methyl-6-(M sulfonate)-benzothiazolinone-(2)-hydrazone, wherein M is a positive charge ion providing a stable aqueous salt thereof; and
   an oxidase enzyme or a peroxidase enzyme.

2. The composition according to claim 1 where M is sodium, potassium or ammonium ion.

3. A composition according to claim 1 further comprising 8-anilino-1-naphthalenesulfonate.

4. A composition according to claim 1 further comprising N-(3-sulfopropyl)analine.

5. A device for testing the presence or concentration of an analyte in a fluid sample comprising:
   a support member,
   a composition positioned on or impregnated in said support said composition comprising a composition for a dry chemistry reagent indicator comprising 3-Methyl-6-(M sulfonate)-benzothiazolinone-(2)-hydrazone, wherein M is a positive charge ion providing a stable aqueous salt thereof, and an oxidase enzyme or a peroxidase enzyme;
   whereby the support member is adapted for receiving a fluid sample such that the fluid sample contacts said composition and adapted such that the support provides for inspection or reading of the color change produced by said composition after contact with the fluid sample.

6. A device according to claim 5 wherein M is a sodium, potassium or ammonium ion.

7. A device according to claim 5 wherein the indicator further comprises 8-anilino-1-naphthalenesulfonate.

8. A device according to claim 5 wherein the indicator further comprises N-(3-sulfopropyl)analine.

9. A method of testing a fluid for the presence or concentration of an analyte comprising:
   a support member having positioned thereon or impregnated therein said support said composition comprising a composition for a dry chemistry reagent indicator comprising 3-Methyl-6-(M sulfonate)-benzothiazolinone-(2)-hydrazone, wherein M is a positive charge ion providing a stable aqueous salt thereof, and an oxidase enzyme or a peroxidase enzyme;
   whereby the support member is adapted for receiving a fluid sample such that the fluid sample contacts said composition and adapted such that the support provides for inspection or reading of the color change produced by the by said composition after contact with the fluid sample;
   applying a fluid sample to said support member and contacting the fluid sample with said composition; and
   reading or measuring the color indication provided by the said composition after contact with said fluid sample.

10. A method according to claim 9 wherein M is a sodium, postassium or ammonium ion.

11. A method according to claim 9 wherein the indicator further comprises 8-anilino-1-naphthalenesulfonate.

12. A method according to claim 9 further comprising N-(3-sulfopropyl)analine.

13. A compound which is 3-Methyl-6-(M sulfonate)-benzothiazolinone-(2)-hydrazone, wherein M is a positive charge ion providing a stable aqueous salt thereof.

14. A compound according to claim 13 wherein M is a sodium, potassium or ammonium ion.

* * * * *